(12) United States Patent
Kao (10) Patent No.: US 9,968,375 B2
(45) Date of Patent: May 15, 2018

(54) CHILDBIRTH AID

(71) Applicant: Ghi-Hwei Kao, Taipei (TW)

(72) Inventor: Ghi-Hwei Kao, Taipei (TW)

(*) Notice: Subject to any disclaimer, the term of this patent is extended or adjusted under 35 U.S.C. 154(b) by 322 days.

(21) Appl. No.: 14/798,755

(22) Filed: Jul. 14, 2015

(65) Prior Publication Data
US 2017/0014160 A1    Jan. 19, 2017

(51) Int. Cl.
*A61G 13/00*   (2006.01)
*A61G 13/12*   (2006.01)
(Continued)

(52) U.S. Cl.
CPC .......... *A61B 17/42* (2013.01); *A61G 13/0009* (2013.01); *A47C 20/025* (2013.01); *A61G 13/125* (2013.01)

(58) Field of Classification Search
CPC ...... A61G 7/065; A61G 7/0755; A61G 7/015; A61G 13/0009; A61G 13/12; A61G 13/1245; A61G 13/125; A61G 13/0018; A61G 13/105; A61G 15/002; A61G 15/005; A61G 2200/12; A61G 2200/38; A61G 2200/36; A61G 2200/34; A61B 17/42; A61B 5/0079; A61B 5/6892; A47C 19/022; A47C 20/025; A47C 20/022; A47C 20/021; A47C 21/00; A47C 21/022; A47C 20/024; A47C 16/00; A47C 16/005; A47C 16/02; A47C 16/025; A47C 16/04; A47C 3/16; A47C 15/008; A47K 17/028; A61H 19/50; A63B 2023/006; A63B 2023/0411; A63B 23/0429
(Continued)

(56) References Cited

U.S. PATENT DOCUMENTS 1,692,943 A * 11/1928 Lelyveld ............... A43D 1/025
                                                                    359/872
2,056,075 A *  9/1936 Roland ................ A47C 16/025
                                                                    297/185
(Continued)

FOREIGN PATENT DOCUMENTS

CN    202386913 U  *  8/2012
CN    204863843 U  * 12/2015

OTHER PUBLICATIONS

Definition of bed. Webster dictionary online, https://www.merriam-webster.com/dictionary/bed, p. 1 definiton 1a.*
(Continued)

*Primary Examiner* — Alireza Nia
*Assistant Examiner* — Rachel Berezik
(74) *Attorney, Agent, or Firm* — Rosenberg, Klein & Lee (57) ABSTRACT

A childbirth aid includes a base panel, two ankle-supporting blocks bilaterally located at a top wall of the base panel for supporting the ankles of a pregnant woman to keep the body center of gravity of the pregnant woman in line with the fulcrum of the mechanism of each foot of the pregnant woman, each ankle-supporting block having a planar top surface and an inclined surface downwardly extended from the planar top surface to the top wall of the base panel, and a gap defined between the two ankle-supporting blocks for the mounting of a safety mirror or anti-collision elastic net selectively in a detachable manner.

14 Claims, 10 Drawing Sheets

(51) Int. Cl.
  *A61B 17/42* (2006.01)
  *A47C 20/02* (2006.01)

(58) Field of Classification Search
  USPC ... 5/602, 603, 606, 618, 624, 631, 647, 648,
   5/649, 651; 297/68, 70, 185, 187,
   297/188.01, 188.05–188.06, 423.1,
   297/423.16–423.17, 423.39, 423.41;
   482/8, 51, 52
  See application file for complete search history.

(56) References Cited

U.S. PATENT DOCUMENTS

| | | | | |
|---|---|---|---|---|
| 4,180,062 A | * | 12/1979 | Alberti | A61B 5/02411 |
| | | | | 297/16.1 |
| 4,713,846 A | * | 12/1987 | Hodroski, Jr. | A47K 17/00 |
| | | | | 4/254 |
| 4,821,350 A | * | 4/1989 | Feldt | A61G 13/0009 |
| | | | | 5/602 |
| 4,823,418 A | * | 4/1989 | Downs | A61B 17/42 |
| | | | | 182/138 |
| 4,973,034 A | * | 11/1990 | Michele | A61G 13/009 |
| | | | | 5/617 |
| 5,043,852 A | * | 8/1991 | Gerstenberger | A47G 1/24 |
| | | | | 362/129 |
| 5,504,953 A | * | 4/1996 | Singer-Leyton | A47C 20/025 |
| | | | | 5/631 |
| 5,507,050 A | * | 4/1996 | Welner | A61G 13/0009 |
| | | | | 5/600 |
| 6,047,420 A | * | 4/2000 | Priester, III | A47C 16/00 |
| | | | | 5/632 |

OTHER PUBLICATIONS

Definition of notch. Oxford dictionary online, https://en.oxford-dictionaries.com/definition/notch, p. 1 definition 1.*
"Integral" definition. Dictionary.com, http://www.dictionary.com/browse/integral?s=t, see attached NPL, p. 2 definition 3.*

* cited by examiner

CHILDBIRTH AID

BACKGROUND OF THE INVENTION

1. Field of the Invention

The present invention relates to childbirth technologies and more particularly, to a childbirth aid, which helps the pregnant woman to give birth in squatting position, enhancing stable body equilibrium and speeding the birthing.

2. Description of the Related Art

Childbirth is one of the important things in life. The arrival of a new baby can bring you joy and happiness, but the mother has to tolerate physical and mental suffering. A bit careless can lead to maternal or fetal life risk, therefore, the process of childbirth is considerably important.

Normally, in the labor process, the expectant women, her companion and obstetric caregivers are considered to be the most watched stage (Motherhood & Newborn Health, 2012). This stage determines the pregnant women to take natural childbirth or to use an equipment for assisting the delivery. Natural childbirth gives an affirmation of self-ability to the pregnant woman. A prolonged birth pushing time can be due to that the fetus is too large, the pregnant woman is unable to give force or gives force in a wrong way, or the pelvic inlet and outlet (birth canal) is not open. In order to let the pregnant woman and health care workers finish the childbirth earlier, a caesarean section can then be selected.

For decades, to reduce the caesarean section rate, many documents discuss the importance of support in delivery, freedom of movement and birth pushing in upright position for promoting women's physical and metal comfort and accelerating the delivery process in a smooth manner (Walker et al., 2012; Zhang Su-Juan, 2005; Huang Jing-Fen, 2011). Fraser and Cooper (2009) indicated four key factors for safety delivery, including: uterine contractions, decreased fetal head, the degree of rotation, and flexion. The fetal and maternal well-being condition and the birth pushing position will affect the strength of uterine contractions. Applying birth pushing in upright position, more particularly, squatting position is more likely to compress the end of the uterus, to force the cervix to dilate, to enhance and promote the strength of uterine contractions, and to assist fetal head drop (Lawrence, Lewis, Hofmeyr, Dowswell, & Styles, 2009; P. P. Simkin & O'Hara, 2002; Penny Simkin & Ancheta, 2011), thereby shortening the delivery process and obtaining more satisfying childbirth experience (Thornton, 1996; Zhang Su-Juan, 2005). Further, giving birth in this manner has less pain, can significantly reduce perineal lacerations and the chance of episiotomy surgery (Gould, 2000). Applying birth pushing in upright position has less concern with abnormal fetal heart tones, the first five minutes after birth, Apgar scores less than seven points, the rate of neonatal emergency (Gardosi, Hutson, & C, 1989; Menticoglou, Manning, Harman, & Morrison, 1995; Nasir, Korejo, & Noorani, 2007).

Nasir et al (2007) discovered that pregnant women would prefer childbirth in squatting position rather than lying position for the sake of ease of birth pushing, although squatting position is difficult to maintain, and also discovered that changing from lying position to squatting position facilitates pregnant women to render force in pushing the fetus if the child birth process slows down. Further, as indicated in literature studies, when the soles of the feet are closely attached to the floor during squatting, prolonged squatting can increase the load of the leg muscles, leading to an uncomfortable feeling (Sriwarno, Shimomura, Iwanaga, & Katsuura, 2008). Therefore, it is recommend that nurses facing the childbirth process should continuously provide support to pregnant women physically as well as emotionally (Mayberry, Strange, Suplee, & Gennaro, 2003), maternal obstetric caregivers should also let pregnant women know the influence of accurate birth pushing position on mother and newborn. Master's thesis in Taiwan, Zhang Su-Juan (2005), discussed the effect of upright position pushing method in second stage of labor and Master's thesis in Taiwan, Chen Su-Xian (1998), discussed effects of Posture Education Program on Women"s Pain Perception and Self-Efficacy during Labor. These master's theses do not individually make a research on squatting related achievements of the labor force. The study of the invention is to provide a childbirth aid for helping all mothers in birth pushing, improving birth pushing effectiveness and self-efficacy and reducing the risk of maternal and neonatal complications and maternal pain.

In the delivery room, most primipara gave birth in a lying position, half-lying position, or side-lying position. A mother giving birth in a lying position, half-lying position, or side-lying position will spend a long hard time, and the pregnant mother may give up natural childbirth and select caesarean section. The birth pushing position affects the result of childbirth. Birth pushing in a lying position will maintain a 30 degree angle between the pelvis and the spine, keeping the fetal head far from the pelvic inlet. Further, in a lying position, the body weight of the pregnant woman is concentrated on the sacrum and the coccyx, impeding the declination of the fetal head, causing the risk of bone pressure, nerve damage and blood clots in the limbs during childbirth. Childbirth with vertical force is recommended by many experts. In human anatomy, childbirth in an upright position can increase the diameter of the pelvic inlet and outlet, enabling the pelvic angle to be maintained in the range of 90 degrees to 120 degrees. Further, the effect of gravity during childbirth in an upright position helps the first exposed portion of the fetus to enter the pelvic inlet, accelerating delivery. In childbirth with vertical force, the best birthing position is squatting. Giving birth while squatting can expand the pelvic outlet about 25%, and can also shorten labor.

Figure 6:
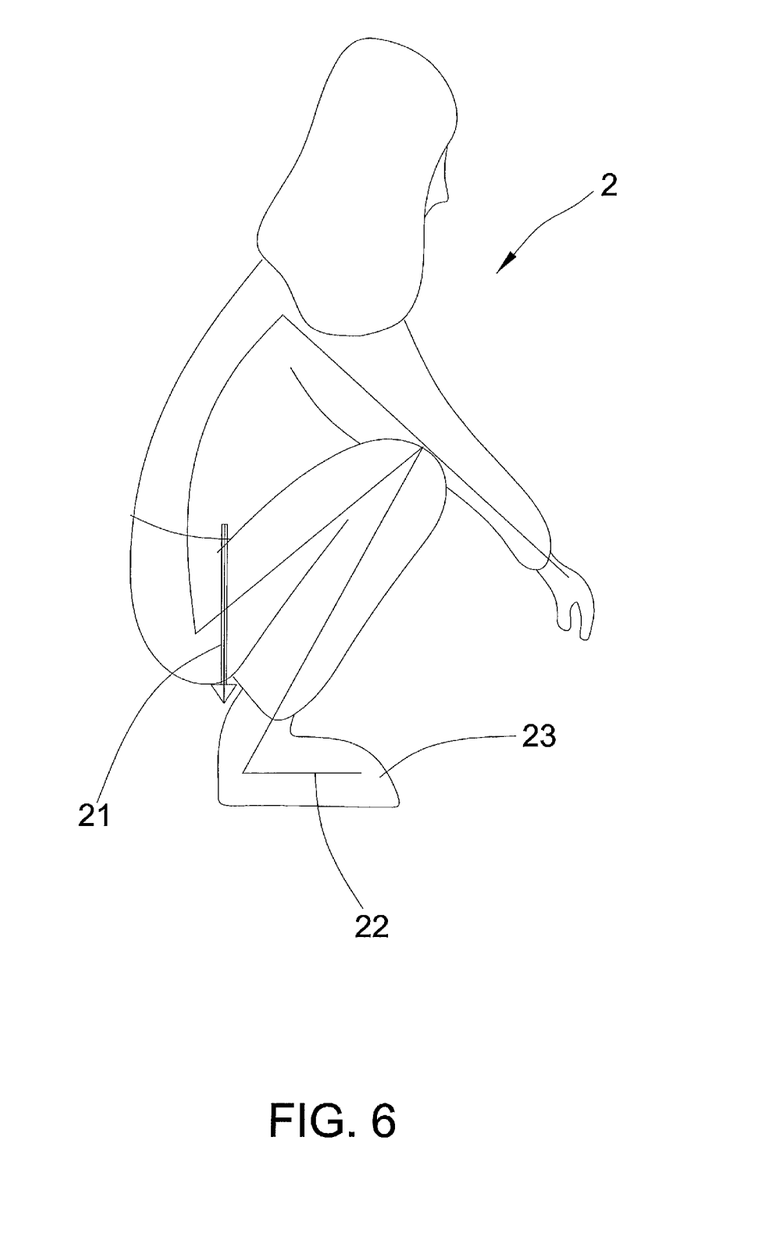
FIG. 6 is schematic drawing illustrating the body center of gravity of a squatted woman disposed behind the fulcrum of the mechanism of each foot.

Further, giving birth in squatting has less pain, can reduce the use of analgesics, give comfort, help increase fetal blood oxygen and reduce fetal blood carbon dioxide, and can also significantly reduce perineal lacerations, the chance of episiotomy surgery or the use of an auxiliary equipment. However, a woman cannot independently sustain a squat for long. When one is squatting, the body center of gravity is disposed behind the fulcrum of the mechanism of the foot, as shown in FIG. 6, and a transverse bar or pad must be provided to give a support.

SUMMARY OF THE INVENTION

The present invention has been accomplished under the circumstances in view. It is therefore the main object of the present invention to provide a childbirth aid, which helps the pregnant woman to give birth in squatting position, enhancing stable body equilibrium and speeding the birthing.

To achieve this and other objects of the present invention, a childbirth aid comprises a base panel, two ankle-supporting blocks bilaterally located at the top wall of the base panel and raised above the top wall of the base panel at a predetermined height for supporting the ankles of a pregnant woman to keep the body center of gravity of the pregnant woman in line with the fulcrum of the mechanism of each foot of the pregnant woman, each ankle-supporting block comprising a planar top surface and an inclined surface downwardly extended from one side of the planar top surface to the top wall of the base panel, a gap defined between the two ankle-supporting blocks, a safety mirror selectively detachably mountable in the gap, and an anti-collision elastic net selectively detachably mountable in the gap.

BRIEF DESCRIPTION OF THE DRAWINGS

FIG. 4-1 illustrates a pregnant woman squatted on the inclined surfaces of the ankle-supporting blocks of the childbirth aid shown in FIG. 4 with the feet splayed.

FIG. 5-1 corresponds to FIG. 5 when viewed from another angle.

FIG. 7-1 is an exploded view illustrating the relationship between an anti-collision elastic net and the gap in the base panel between the two ankle-supporting blocks of the childbirth aid.

FIG. 7-2 is a schematic sectional view illustrating the retaining notches of the mounting frame of the safety mirror/anti-collision elastic net engaged with the respective retaining rod of the base panel.

DETAILED DESCRIPTION OF THE PREFERRED EMBODIMENT

Figure 1:
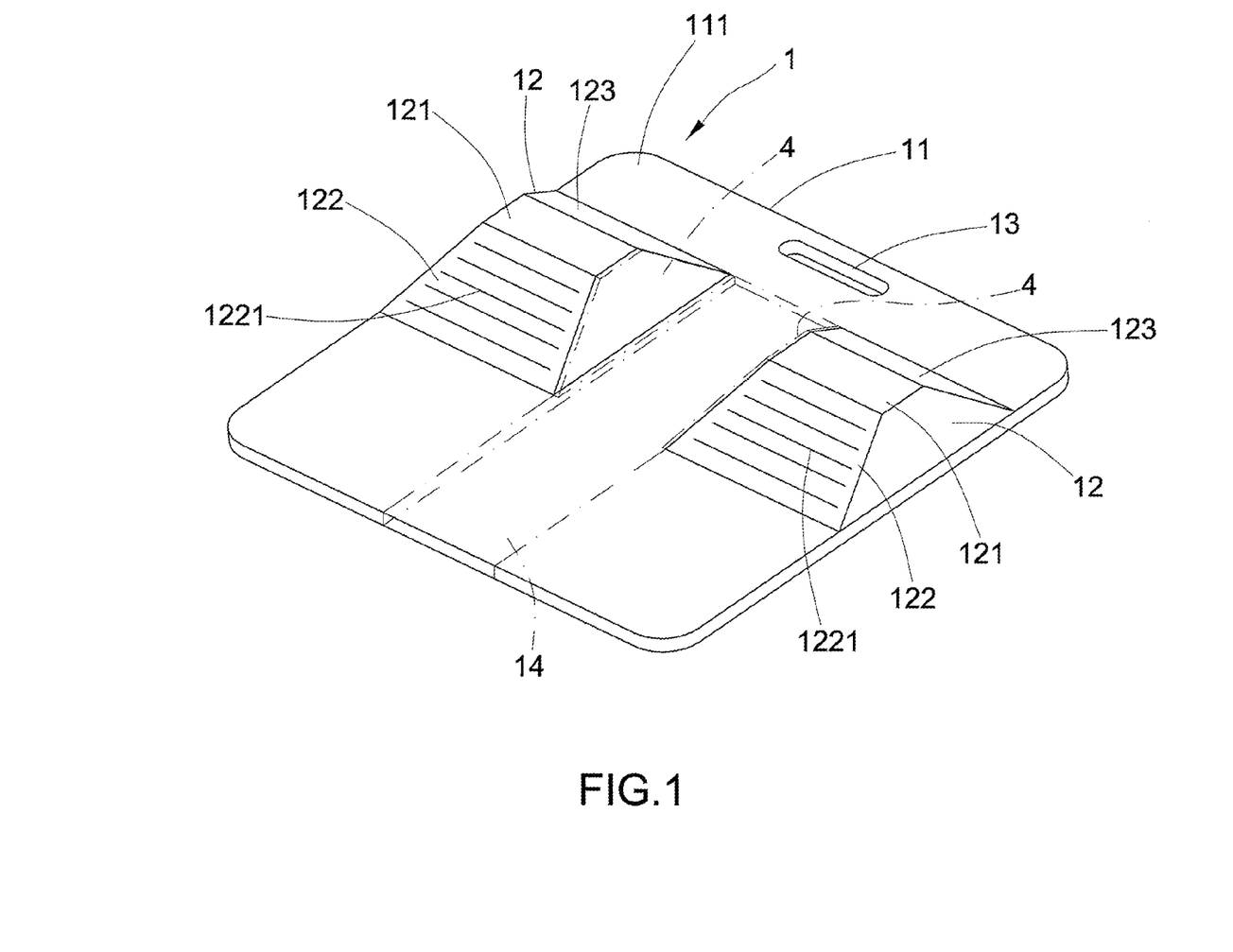
FIG. 1 is a schematic elevational view of a childbirth aid in accordance with the present invention.
Figure 2:
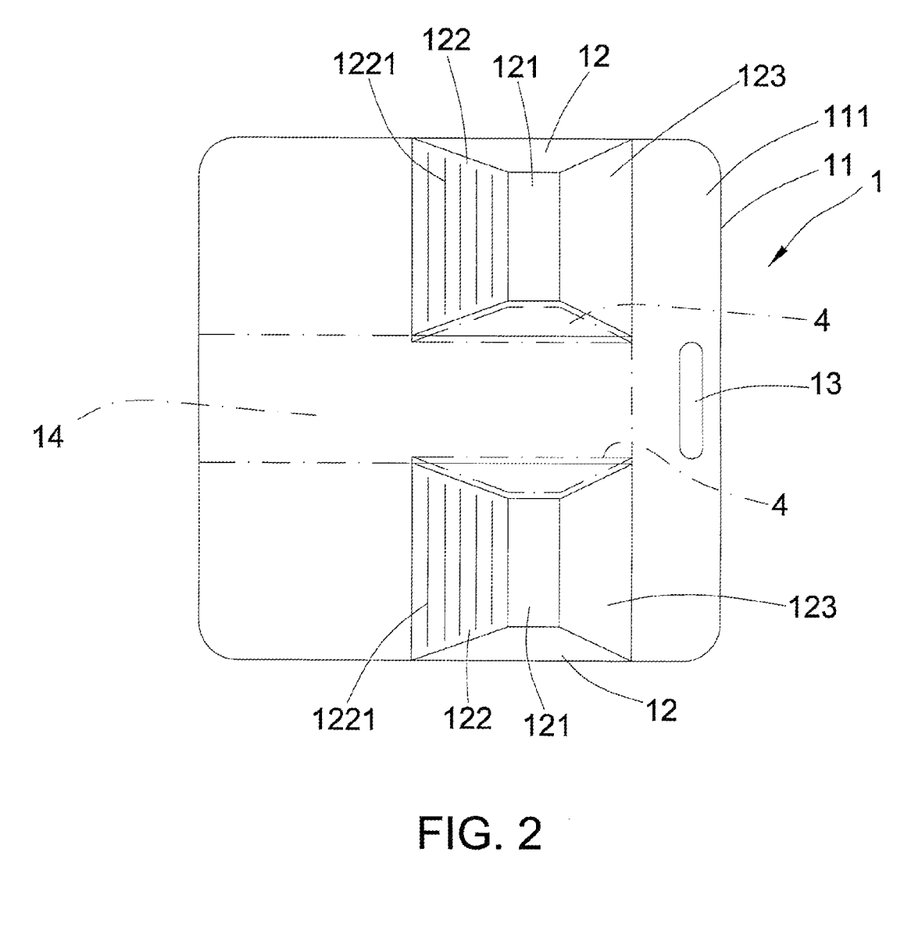
FIG. 2 is a top view of the childbirth aid in accordance with the present invention.
Figure 3:
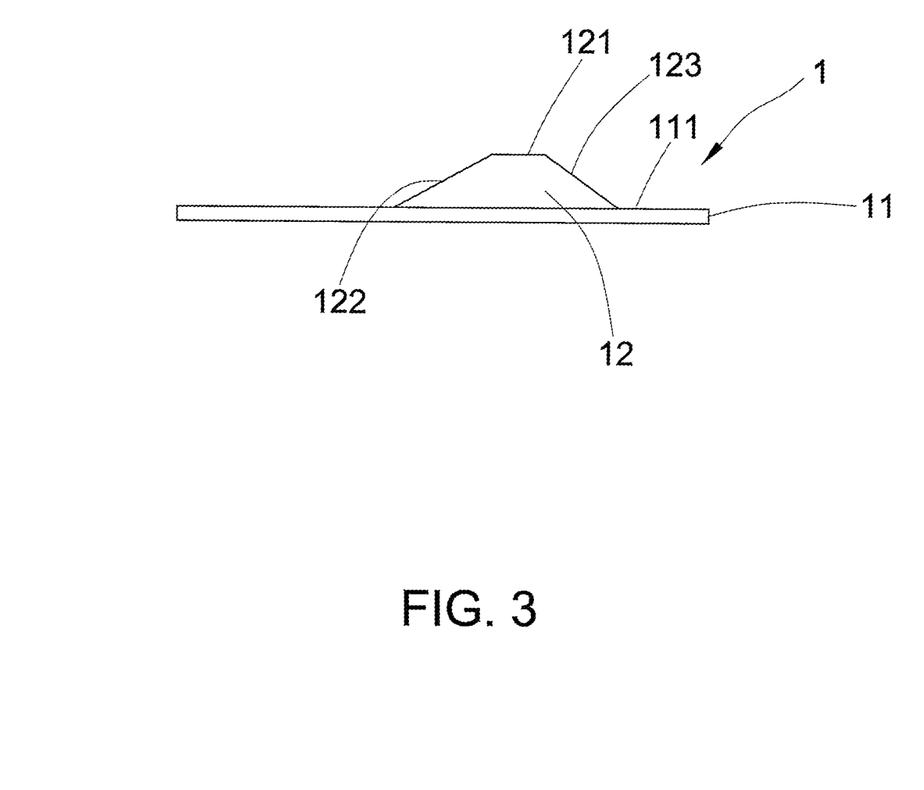
FIG. 3 is a side view of the childbirth aid in accordance with the present invention.
Figure 5:
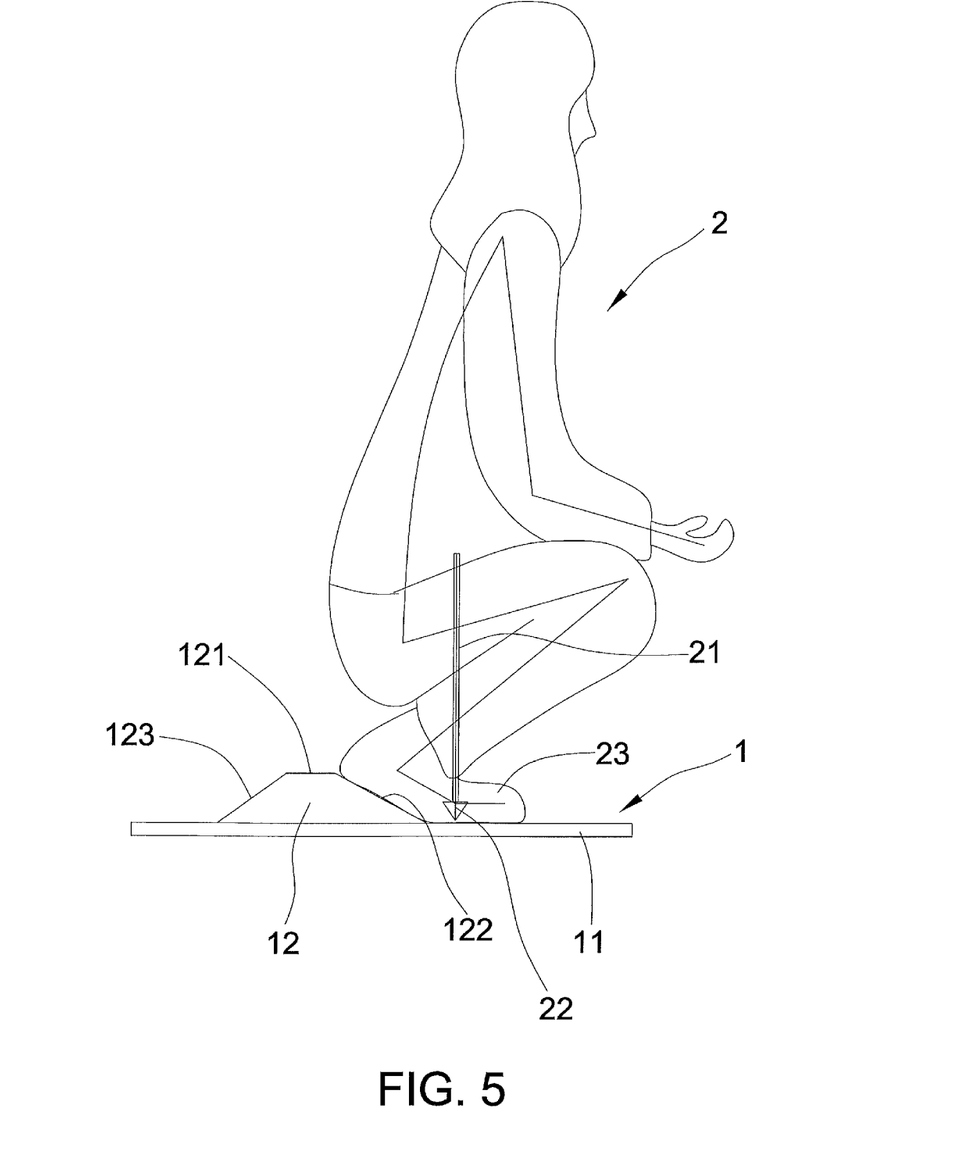
FIG. 5 is a schematic drawing illustrating the body center of gravity of the pregnant woman at the childbirth aid in line with the fulcrum of the mechanism of the foot.

Referring to FIGS. 1-3, a childbirth aid (1) in accordance with the present invention is shown. The childbirth aid (1) comprises a base panel (11), and two ankle-supporting blocks (12) disposed on a top surface (111) of the base panel (11). Each ankle-supporting block (12) defines an inclined surface (122). When a pregnant woman (2) using the childbirth aid (1) is giving birth in squatting position (see FIG. 5), the ankle-supporting blocks (12) give support to the ankles of the pregnant woman (2). By means of the inclined surfaces (122) of the ankle-supporting blocks (12), the body center of gravity (21) of the pregnant woman (2) is shifted, keeping the body center of gravity (21) of the pregnant woman (2) in line with the fulcrum of the mechanism of each foot (22) of the pregnant woman (2), enhancing stable body equilibrium and providing a high degree of freedom. Birthing in squatting enlarges the diameter of the pelvic inlet and outlet of the pregnant woman (2). Further, the effect of gravity also helps the first exposed portion of the fetus enter the pelvic inlet, speeding the birthing.

Figure 7:
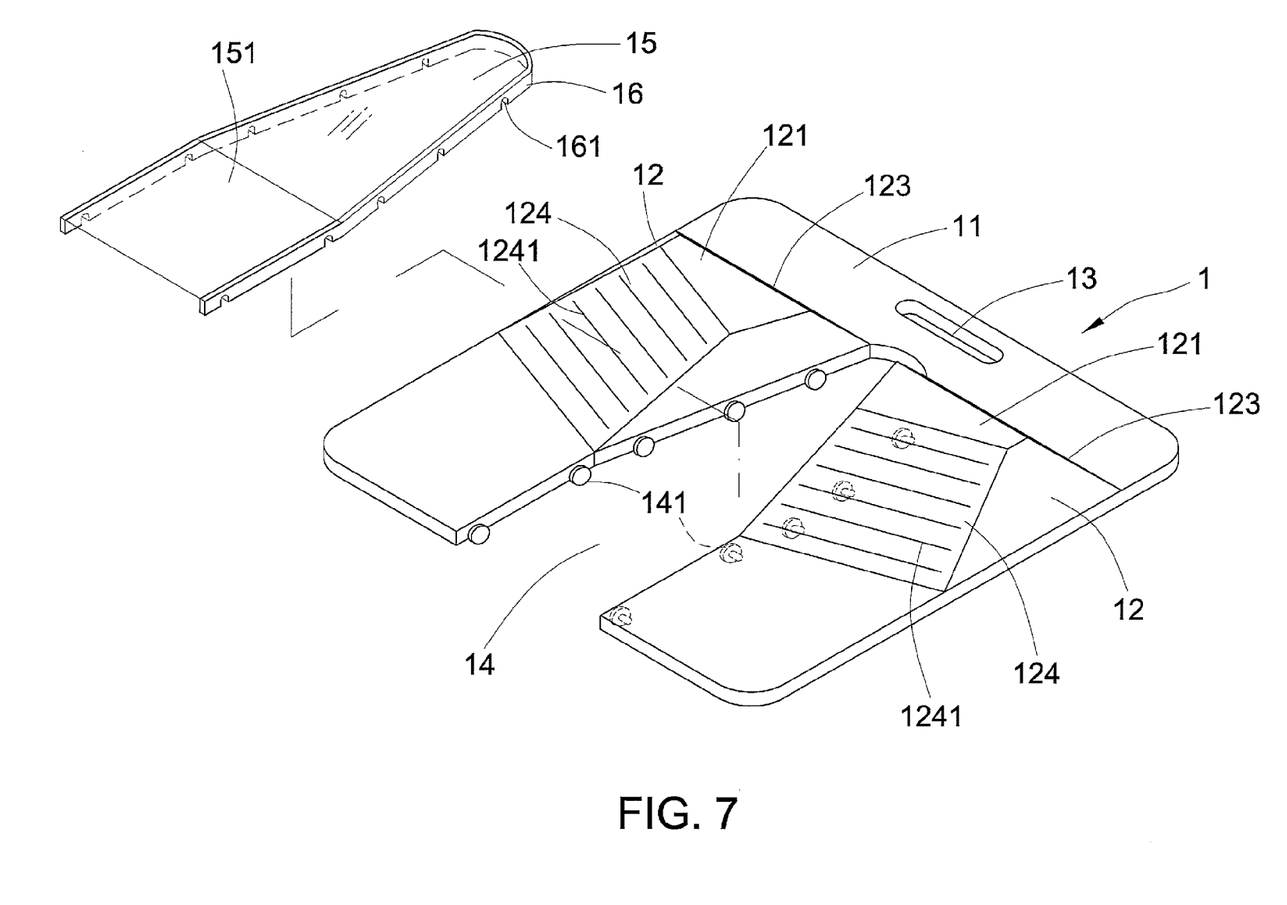
FIG. 7 is an exploded view illustrating the relationship between a safety mirror and the gap in the base panel between the two ankle-supporting blocks of the childbirth aid.

Further, the two ankle-supporting blocks (12) are bilaterally mounted on the top surface (111) of the base panel (11) and raised above the top surface (111) of the base panel (11) at a predetermined height. Preferably, each ankle-supporting block (12) comprises a planar top surface (121), and at least one inclined surface (122), or in the depicted example of FIG. 1, front and rear inclined surfaces (122)(123) respectively downwardly sloping from opposing front and rear sides of the planar top surface (121) of the ankle-supporting block (12) to the top surface (111) of the base panel (11). The height of the ankle-supporting block (12) and the slopes of the front and rear inclined surfaces (122)(123) are adjusted according to the body size and body height of the pregnant woman (2). Further, a gap (14) is defined in the base panel (11) between the two ankle-supporting blocks (12). A safety mirror (15) (see FIG. 7) or anti-collision elastic net (3) (see FIG. 7-1) can be detachably mounted in the gap (14), facilitating viewing the exposed portion of the fetus outside the vagina of the pregnant woman, avoiding potential birth injuries during labor and delivery, and also facilitating the work of health care personnel in child birthing. Thus, when a pregnant woman (2) uses the childbirth aid (1) for child birthing, the inclined surfaces (122) of the ankle-supporting blocks (12) can shift the body center of gravity (21) of the pregnant woman (2) into alignment with the fulcrum of the mechanism of each foot (22) of the pregnant woman (2) (see FIG. 5 and FIG. 5-1), enhancing stable body equilibrium, reducing physical exertion, enlarging the pelvic inlet and outlet, and letting the pelvic angle be maintained at an angle of 90 degrees to 120 degrees. Further, birthing in squatting can expand the pelvic outlet by about 25%. Further, the effect of gravity also helps the fetus enter the pelvic inlet rapidly, speeding the birthing, reducing pregnant woman discomfort shortening labor and delivery and reducing medical waste. Further, a soft material (4) can be bonded to an inner side of each ankle-supporting block (12) to face toward the gap (14), preventing the baby from collision injuries. Further, the design of the ankle-supporting blocks (12) can be applied to an obstetric delivery bed to form a composite obstetric delivery bed for childbirth in squatting or half-lying position.

Figures 71, 72:
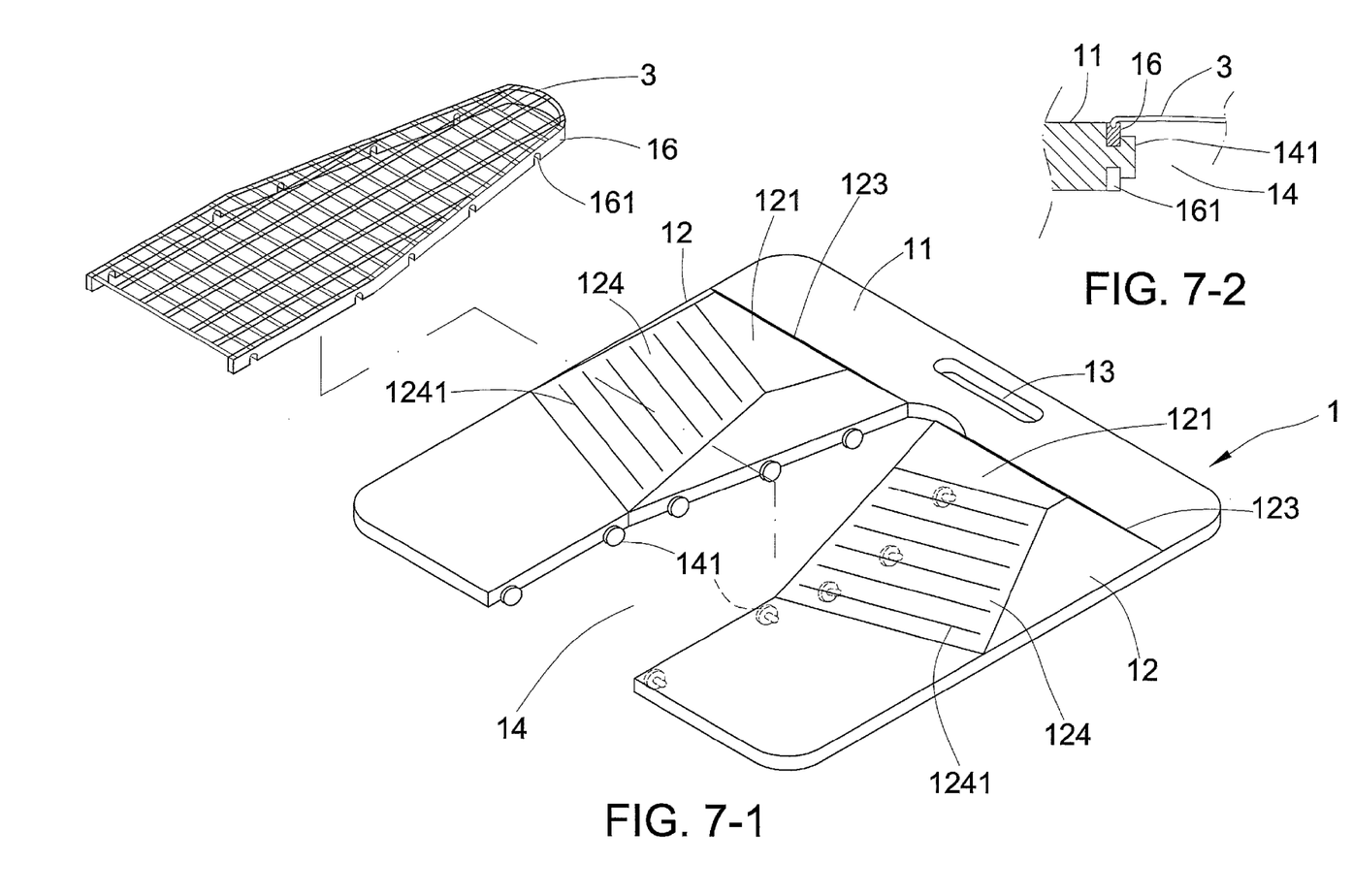

As stated above, the safety mirror (15) or anti-collision elastic net (3) is selectively detachably mountable in the gap (14) in the base panel (11) between the two ankle-supporting blocks (12). The safety mirror (15) or anti-collision elastic net (3) comprise a mounting frame (16) extended around the border thereof, and a plurality of retaining notches (161) spaced along two opposite lateral sides of the mounting frame (16). The base panel (11) further comprises a plurality of retaining rods (141) suspended in the gap (14) at two opposite sides. When setting the mounting frame (16) of the safety mirror (15) or anti-collision elastic net (3) into the gap (14) in the base panel (11), the retaining notches (161) in the mounting frame (16) of the safety mirror (15) or anti-collision elastic net (3) are respectively forced into engagement with the respective retaining rods (141) of the base panel (11) (see FIG. 7-2). Thus, the safety mirror (15) or anti-collision elastic net (3) can be conveniently mounted in or detached from the gap (14) in the base panel (11) (see FIG. 7 and FIG. 7-1). Further, the safety mirror (15) has a flexible panel member (151) at a front side thereof.

Preferably, the inclined surface (122) or (124) of each ankle-supporting block (12) is configured to provide an anti-slip pattern (1221) or (1241) for the positioning of the sole of foot (23) positively positioned. Further, the base panel (11) can be configured to provide a slotted grip portion (13) at, for example, a front side thereof to facilitate carrying.

Figure 4:
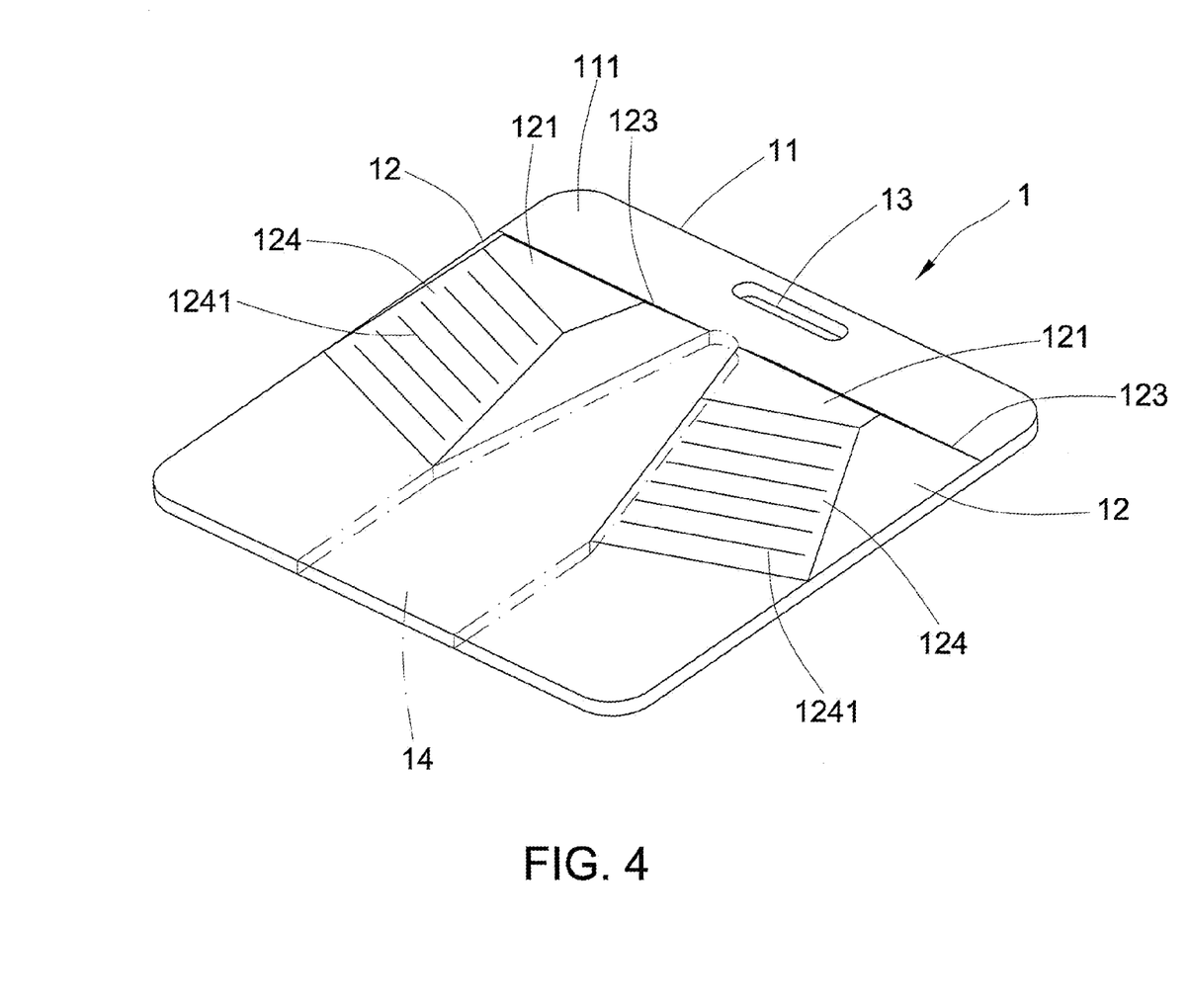
FIG. 4 is a schematic elevational view of an alternate form of the childbirth aid in accordance with the present invention.
Figure 41:
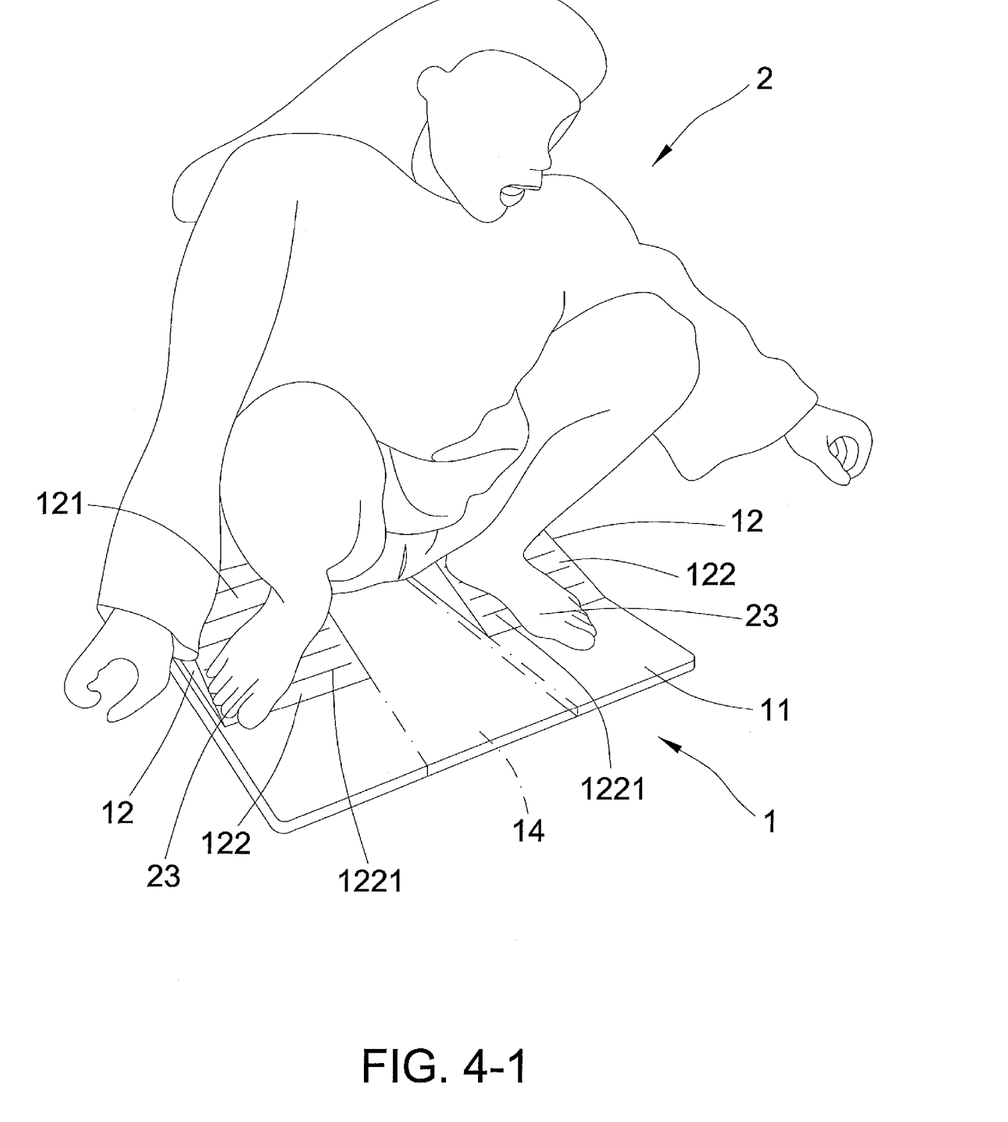
Figure 51:
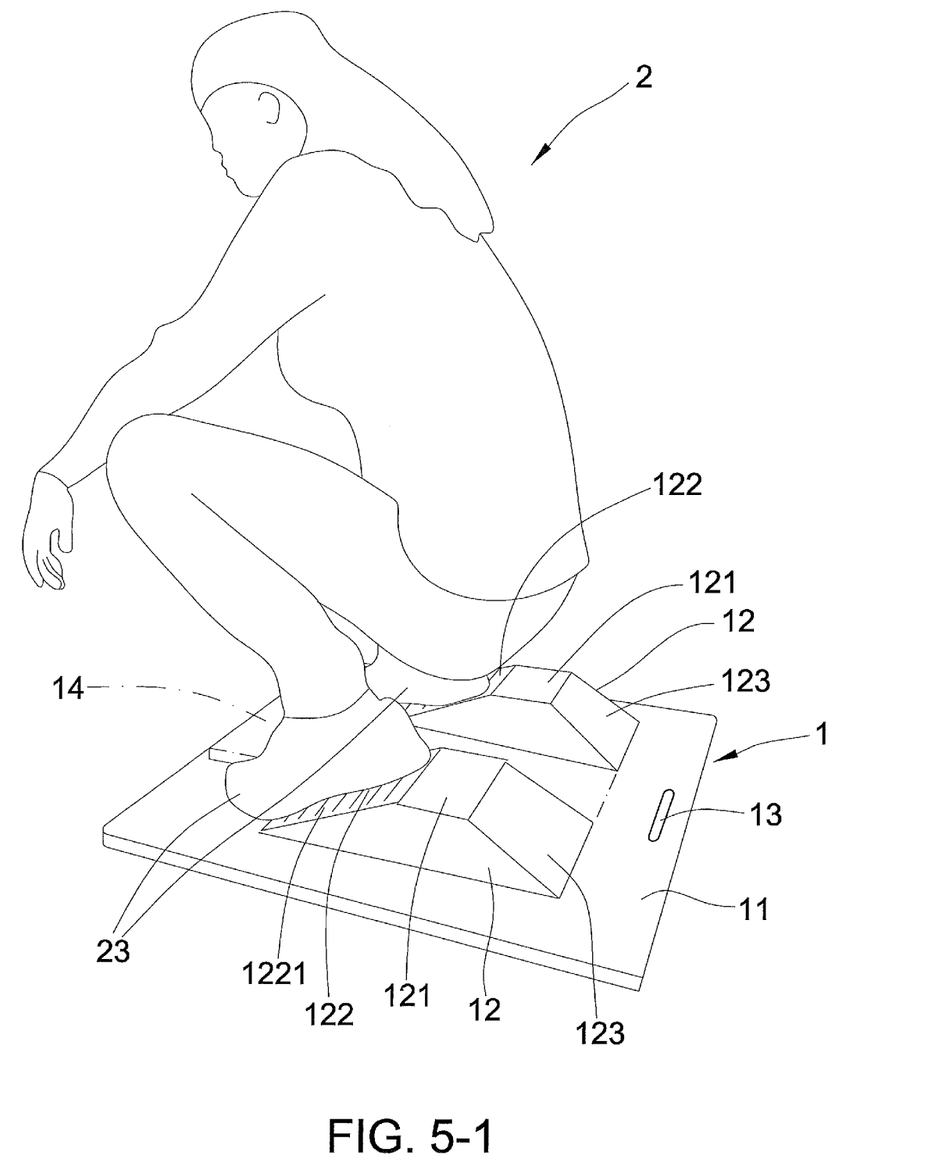

Further, when an ordinary person or pregnant woman is in a squatting position, the feet (23) are splayed out (see FIG. 4-1). Thus, the two ankle-supporting blocks (12) are arranged on the base panel (11) in such a manner that the inclined surfaces of the ankle-supporting blocks (12) are splayed inclined surfaces (124) (see FIG. 4) to fit the user's feet in squatting, preventing leg tingling and numbness.

What the invention claimed is:

1. A childbirth aid, comprising:
    a base panel;
    two ankle-supporting blocks bilaterally disposed on a top surface of said base panel and raised above the top surface of said base panel to a predetermined height, each said ankle-supporting block including a planar top surface and an inclined surface downwardly extended from one side of said planar top surface toward said base panel, each said inclined surface being oriented relative to the top surface of said base panel to form a cradling structure for a bent foot of a pregnant woman, the cradling structure thereby guiding the pregnant woman's foot to define a fulcrum point and maintaining a center of gravity of the pregnant woman's body when in a squatting position in vertical alignment with the fulcrum point;
    a gap defined in said base panel between said two ankle-supporting blocks; and
    an anti-collision elastic net selectively detachably mountable in said gap.

2. The childbirth aid as claimed in claim 1,
    wherein said base panel includes a plurality of retaining rods suspended in said gap at two opposite sides between said ankle-supporting blocks; and
    wherein said anti-collision elastic net includes:
        a mounting frame extended around a border thereof, and
        a plurality of retaining notches spaced along two opposite lateral sides of said mounting frame and respectively detachably engageable with respective said retaining rods of said base panel.

3. The childbirth aid as claimed in claim 1, wherein the height of said ankle-supporting blocks and a slope of said inclined surface are determined according to a body size and body height of the pregnant woman.

4. The childbirth aid as claimed in claim 1, wherein said inclined surface of each said ankle-supporting block is configured to provide an anti-slip pattern.

5. The childbirth aid as claimed in claim 1, wherein said gap defined in said base panel between the inclined surfaces of said two ankle-supporting blocks has a width gradually increasing in direction from a rear side of said base panel toward an opposing front side thereof.

6. The childbirth aid as claimed in claim 1, further comprising a soft material bonded to an inner side of each said ankle-supporting block.

7. The childbirth aid as claimed in claim 1, wherein each said inclined surface is splayed toward an edge of said base panel.

8. The childbirth aid as claimed in claim 1, wherein said base panel and said ankle-supporting blocks are integrally formed.

9. A childbirth aid, comprising:
    a base panel;
    two ankle-supporting blocks bilaterally disposed on a top surface of said base panel and raised above the top surface of said base panel to a predetermined height, each said ankle-supporting block including a planar top surface and an inclined surface downwardly extended from one side of said planar top surface toward said base panel, each said inclined surface being oriented relative to the top surface of said base panel to form a cradling structure for a bent foot of a pregnant woman, the cradling structure thereby guiding the pregnant woman's foot to define a fulcrum point and maintaining a center of gravity of the pregnant woman's body when in a squatting position in vertical alignment with the fulcrum point;
    a gap defined in said base panel between said two ankle-supporting blocks; and
    a safety mirror selectively detachably mountable in said gap.

10. The childbirth aid as claimed in claim 9,
    wherein said base panel includes a plurality of retaining rods suspended in said gap at two opposite sides between said ankle-supporting blocks; and
    wherein said safety mirror includes:
        a mounting frame extended around a border thereof, and
        a plurality of retaining notches spaced along two opposite lateral sides of said mounting frame and respectively detachably engageable with respective said retaining rods of said base panel.

11. The childbirth aid as claimed in claim 9, wherein the height of said ankle-supporting blocks and a slope of said inclined surface are determined according to a body size and body height of the pregnant woman.

12. The childbirth aid as claimed in claim 9, wherein said inclined surface of each said ankle-supporting block is configured to provide an anti-slip pattern.

13. The childbirth aid as claimed in claim 9, wherein said gap defined in said base panel between the inclined surfaces of said two ankle-supporting blocks has a width gradually increasing in direction from a rear side of said base panel toward an opposing front side thereof.

14. The childbirth aid as claimed in claim 9, further comprising a soft material bonded to an inner side of each said ankle-supporting block.

* * * * *